United States Patent [19]
Cohen et al.

[11] Patent Number: 5,506,103
[45] Date of Patent: Apr. 9, 1996

[54] METHOD FOR DETECTING CHARGED OLIGONUCLEOTIDES IN BIOLOGICAL FLUIDS

[75] Inventors: Aharon S. Cohen, Brookline; Andre Bourque, Marlboro, both of Mass.

[73] Assignee: Hybridon, Inc., Worcester, Mass.

[21] Appl. No.: 153,365

[22] Filed: Nov. 16, 1993

[51] Int. Cl.$^6$ .......................... C12Q 1/68; G01N 33/53; C07H 21/00
[52] U.S. Cl. ............................ 435/6; 435/7.92; 536/25.4
[58] Field of Search ........................ 435/6, 7.92; 536/25.4

[56] References Cited

U.S. PATENT DOCUMENTS

| | | | |
|---|---|---|---|
| 4,816,571 | 3/1989 | Andrus et al. | 536/23.1 |
| 4,965,349 | 10/1990 | Woo et al. | 536/25.31 |
| 5,047,524 | 9/1991 | Andrus et al. | 536/25.31 |
| 5,262,530 | 11/1993 | Andrus et al. | 536/25.31 |

OTHER PUBLICATIONS

Agrawal et al. (1992) *Trends Biotech.* 10:152–158.
Bjoualsan et al, *Appl. Environ. Microbiol* 54:2852–2855 (1988).
Agrawal et al., *PNAS* 88:7595–7599 (1991).
Derwent Abstract EP507591 (1992).
Drager et al., *Anal. Biochem* 145:47–56 (1985).
Southern (1975) *J. Mol. Biol.* 98:503–517.
Righetti et al. (1977) *J. Chromatog.* 137:171–181.
Artoni et al. (1984) *Anal. Biochem.* 137:420–428.
Dovichi et al. (1984) *Anal. Chem.* 56:348–354.
Vecchio et al. (1984) *Anal. Biochem.* 137:410–419.
Zamecnik et al. (1986) *Proc. Natl. Acad. Sci.* (USA) 83:4143–4147.
Agrawal et al. (1988) *Proc. Natl. Acad. Sci.* (USA) 85:7079–7083.
Cheng et al. (1988) *Science* 242:562–564.
Cohen et al. (1988) *Proc. Natl. Acad. Sci.* (USA) 85:9660–9663.
Goodchild et al. (1988) *Proc. Natl. Acad. Sci.* (USA) 85:5507–5511.
Matsukura et al. (1988) *Gene* 72:343–347.
Sarin et al. (1988) *Proc. Natl. Acad. Sci.* (USA) 85:9660–9664.
Agrawal et al. (1989) *Proc. Natl. Acad. Sci.* (USA) 86:7790–7794.
Matsukura et al. (1989) *Proc. Natl. Acad. Sci.* (USA) 86:4244–4248.
Current Protocols in Molecular Biology (Ausubel et al., eds.) John Wiley & Sons, New York (199) 2:2.2.
Agrawal in *Prospects for Antisense Nucleic Acid Therapy for Cancer and AIDS*, (Wickstrom, ed.) Liss, New York (1991) pp. 143–158.
Vickers et al. (1991) *Nucleic Acid Res.* (USA) 19:3359–3368.
Agrawal et al. in *Gene Regulation: Biology of Antisense RNA and DNA* (Erickson and Izant, eds.) Raven Press Ltd., New York (1992) pp. 273–283.
Matsukura et al. in *Prospects for Antisense Nucleic Acid Therapy of Cancer and AIDS*, Wiley–Liss, (USA) (1991) pp. 152–158.
Metelev et al. (1992) *Anal. Chem.* 72:342–346.
Pompon et al. (1992) *Bichem. Pharm.* 43:9660–9664.
Bourque et al. (1992) *J. Chromatography* 617:7790–7794.
Cohen et al. (1993) *J. Chromatog.* 638:4244–4248.
Cohen et al. (1993) *Trends Anal. Chem.* 12:195–202.
Temsamani et al. (1993) *Anal. Biochem.* (in press).

*Primary Examiner*—W. Gary Jones
*Assistant Examiner*—Eggerton Campbell
*Attorney, Agent, or Firm*—Lappin & Kusmer

[57] ABSTRACT

Disclosed is a method for detecting and quantitating oligonucleotides with charged internucleotide linkages in biological fluids. In this method, a biological fluid sample is contacted with an anion exchange resin at from 40° C. to 65° C. for a time sufficient to enable oligonucleotides in the sample to adsorb to the resin. The absorbed oligonucleotides are then desorbed with a buffer having a salt concentration of about 1 M to 2.5 M and a pH in the range of about 6.5 to 7.5, the desorption being performed at about 40°–65° C. The oligonucleotides so released are then detected and quantitated.

16 Claims, 4 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:1:

CTCTCGCACC CATCTCTCTC CTTCT 25

METHOD FOR DETECTING CHARGED OLIGONUCLEOTIDES IN BIOLOGICAL FLUIDS

BACKGROUND OF THE INVENTION

This invention relates to the detection of nucleic acids. More particularly, this invention relates to the detection and quantitation of charged nucleic acid sequences present in biological fluids.

Detection of specific nucleic acid sequences present in cells is generally known in the art. Southern (*J. Mol. Bio.* (1975) 98: 503–517) teaches the detection of specific sequences among DNA fragments separated by gel electrophoresis using "blotting" or transfer of the DNA fragments to a membrane, followed by hybridization of denatured DNA fragments with a radioactive probe and autoradiography. This procedure has also been extended to the detection of RNA molecules extracted from cells or tissues. More recently, faster and quantitative "dot-blotting" procedures have been developed for rapid detection of DNA or RNA from tissues or cells.

Recently, considerable interest has been generated in the development of synthetic oligonucleotides as therapeutic or gene expression modulating agents in the so-called antisense approach. These agents, called antisense oligonucleotides, bind to a target single-stranded nucleic acid molecule according to the Watson-Crick or the Hoogstein rule of base pairing, and in doing so, disrupt the function of the target by one of several mechanisms: by preventing the binding of factors required for normal translation or transcription; in the case of an mRNA target, by triggering the enzymatic destruction of the message by RNase H; or by destroying the target via reactive groups attached directly to the antisense oligonuceotide.

Antisense oligodeoxynucleotides have been designed to specifically inhibit the expression of HIV-1 and other viruses (see, e.g., Agrawal (1992) *Trends in Biotechnology*10:152–158; Agrawal et al. in *Gene Regulation: Biology of Antisense RNA and DNA* (Erickson and Izant, eds.) Raven Press Ltd., New York (1992) pp. 273–283); Matsukura et al. in *Prospects for Antisense Nucleic Acid Therapy of Cancer and AIDS*, Wiley-Liss, Inc. (1992) pp. 159–178; and Agrawal (1991) in *Prospects for Antisense Nucleic Acid Therapy for Cancer and AIDS*, (Wickstrom, ed. ) Liss, New York, pp. 145–148). For example, it has been shown that antisense oligonucleotides having sequences complementary to portions of genomic HIV-1 ribonucleic acid (RNA) inhibit viral replication in early infected cells (Zamecnik et al. (1986) *Proc. Natl. Acad. Sci.* (*USA*) 83:4143–4147; Goodchild et al. (1988) *Proc. Natl. Acad. Sci* (*USA*) 85:5507–5511).

To further improve their characteristics as antisense agents, chemically modified, nuclease-resistant analogs have been developed which are effective in inhibiting HIV-1 replication in tissue cultures (Sarin et al. (1988) *Proc. NatlAcad. Sci.* (*USA*) 85:7448–7451: Agrawal et al. (1988) *Proc. Natl. Acad. Sci.* (*USA*) 85:7079–7083; Matsukura et al. (1988) *Gene* 72:343–347). These analogs include oligonucleotides with nuclease-resistant phosphorothioate internucleotide linkages shown to inhibit HIV-1 replication in both acute infection (Agrawal et al. (1989) *Proc. Natl. Acad. Sci* (*USA*) 86:7790–7794) and in chronically infected cell lines (Agrawal et al. (1991 ) in *Gene Regulation: Biology of Antisense RNA*, (Erickson et al., eds.) Raven Press, New York, pp. 273–284; Vickers et al. (1991) *Nucleic Acids Res.* 19:3359–3368; Matsukura et al. (1989) *Proc. Natl. Acad. Sci.* (*USA*) 86:4244–4248; Agrawal et al. (1988) *Proc. NatlAcad. Sci.* (*USA*) 85:7079–7083).

For an antisense therapeutic approach to be effective, oligonucleotides must be introduced into a subject and must reach the specific tissues to be treated. Consequently, there is a need to be able to detect oligonucleotides in body fluids or tissues.

Temsamani et al., *Anal. Biochem.* 215:54–58(1993) developed a method of extracting oligonucleotides which had been proteolytically digested from body fluid or tissue samples. Total nucleic acids are precipitated from the extracted samples and transferred to a hybridization membrane where they are hybridized under specific conditions to a labelled oligonucleotide that is complementary to the oligonucleotide that was administered to the subject. Presence of the hybridized, labelled oligonucleotide is then detected by standard procedures.

Radiolabelled oligonucleotides have been administered to animals and their distribution within body fluids and tissues has been assessed by extraction of the oligonucleotides followed by autoradiography (see Agrawal et al. (1991) *Proc. Natl. Acad. Sci.* (*USA*) 88:7595–7599). As a practical matter, however, these methods are not feasible for use in human patients.

Unfortunately, the various techniques for detecting specific unlabelled nucleic acid sequences present in body fluids or tissues has thus far only been extended to polynucleotides such as large DNA or RNA molecules. Due to the small size of antisense oligonucleotides, special problems relating to nonspecific binding or background, as well as to absence of binding, nondetection, or false negatives exist. Thus, there remains a need to develop procedures for the detection of specific synthetic oligonucleotide sequences present in biological fluids such as body fluids and tissues.

SUMMARY OF THE INVENTION

It has been determined that DNA and RNA adhere more strongly to anion exchange resins than do proteins and polypeptides under certain experimental conditions. In addition, it has been discovered that nucleic acids with a more highly charged delocalization (i.e., effective charge on a portion of the molecule) than phosphodiester-containing molecules have a much higher affinity for anion exchange resins than do such phosphodiester-containing molecules. This is because the effective charge on this type of molecule is less than that of a phosphodiester-containing molecule, thereby increasing its stability. These discoveries have been exploited to develop the present invention.

In its broadest aspects, this invention provides a method for detecting and quantitating charged oligonucleotides in biological fluids. As used herein, the term "charged oligonucleotide" encompasses DNA and RNA and hybrid nucleic acids containing both DNA and RNA, nucleic acids with various sugar, phosphate, or base modifications, and nucleic acids having charged internucleotide linkages. In preferred aspects of the invention, the biological fluids monitored for oligonucleotide analog presence include serum, plasma, urine, semen, lacrimal secretions, saliva, cerebrospinal fluid, sweat, synovial fluid, mucous secretions, extracts from plants, bacteria, fungii, animal cells, and tissues. "Tissues" include those constituting any organ such as lymphoid tissue, liver, kidney, brain, intestine, smooth, striated, and cardiac muscle, dermis and epidermis, among others. In some aspects of the invention the method also includes filtering or centrifuging the fluid sample before placing it in contact with the resin.

The method of the invention includes contacting a biological fluid sample with an anion exchange resin for a time sufficient to enable oligonucleotides in the sample to adsorb to the resin. Then, the oligonuclotides are desorbed from the resin with a buffer having a salt concentration of about 1M to 2.5M and a pH in the range of about 6.5 to 7.5. Both the contacting and desorbing steps are performed at about 40° C. to 65° C. Oligonucleotides released from the resin are then detected.

In preferred embodiments of the invention, the biological fluid sample is contacted with an anion exchange resin. A strong anion exchange resin such as a quaternary alkylamine compound is used in one aspect of the invention. The term "strong anion exchange resin" is used herein to denote resins whose charged active site is covalently attached to the surface of the packing and exhibits strongly ionic characteristics such that molecules in contact with the resin and are retained by displacing a counterion that initially associates with the ionic group bound to the surface.

In another embodiment, the biological sample is mixed with a buffered solution having a pH of about pH 6.5 to 9 before being placed in contact with a weak anion exchange resin such as diethylaminoethyl or polyethyleneimine. As used herein, the term "weak anion exchange resin" is meant to encompass a resin whose charged active site exhibits ionic characteristics weaker than those of quaternary alkylamines. In some aspects this buffer has a salt concentration of about 100 mM to 300 mM, and preferably about 250 mM.

In yet another embodiment of the invention, the oligonucleotides adhered to the resin are eluted with a buffer containing a soft anion. As used herein, the term "soft anion" refers to charged molecular or atomic species having a diffuse negative charge due to the large size of its electron shell. Useful examples of salts containing soft anions include bromide, chloride, and thiocyanide. Preferred salts include lithium bromide, lithium chloride, potassium bromide, potassium chloride, ammonium bromide, and ammonium chloride.

In one preferred aspect of the invention the oligonucleotides are eluted from the resin with a buffer comprising 2M salt. Alternatively, a fast salt gradient may be used for desorption purposes. The term "fast salt gradient" as used herein refers to a gradient which flows from its one extreme concentration to its other extreme concentration within about 3 minutes.

The contacting and desorbing steps of the invention may be practiced by subjecting the biological sample to high pressure liquid chromatography (HPLC). Alternatively, the sample may be subjected to solid phase extraction methods which include adhering the charged oligonucleotides to resin in, e.g., a column which is neither automated nor under pressure and then eluting the oligonucleotides by washing the resin with a salt buffer as described above.

Detection of the oligonucleotides released from the resin in either case is accomplished by monitoring UV absorbance at 260 nm in some aspects of the invention. In others, the oligonucleotides are detected by laser induced fluorescence and other spectroscopic methods. In yet other aspects, complementary oligonucleotides containing a detectable marker are hybridized to the eluted oligonucleotides, which are then detected in a manner dependent on the nature of the marker. Preferred markers include radioactive, fluorescent, or chemiluminescent compounds, biotin, or an enzyme having detectable reaction products. The oligonucleotides so detected are then quantitated in some embodiments of the invention.

The method according to the invention is useful for detecting oligonucleotides in tissues and fluids of patients undergoing antisense oligonucleotide therapy or clinical trials thereof, as well as in tissues and fluids of animals used in preclinical studies of oligonucleotide biodistribution and pharmacokinetics.

BRIEF DESCRIPTION OF THE DRAWINGS

The foregoing and other objects of the present invention, the various features thereof, as well as the invention itself may be more fully understood from the following description, when read together with the accompanying drawings in which.

DETAILED DESCRIPTION OF THE PREFERRED EMBODIMENTS

A new and efficient method of determining the concentration and/or presence of charged oligonucleotide analogs in biological fluids and tissues has been devised which is quick, effective, and inexpensive. This method provides quantitative data in only minutes per sample and requires minimal sample handling prior to analysis.

Figure 1A:
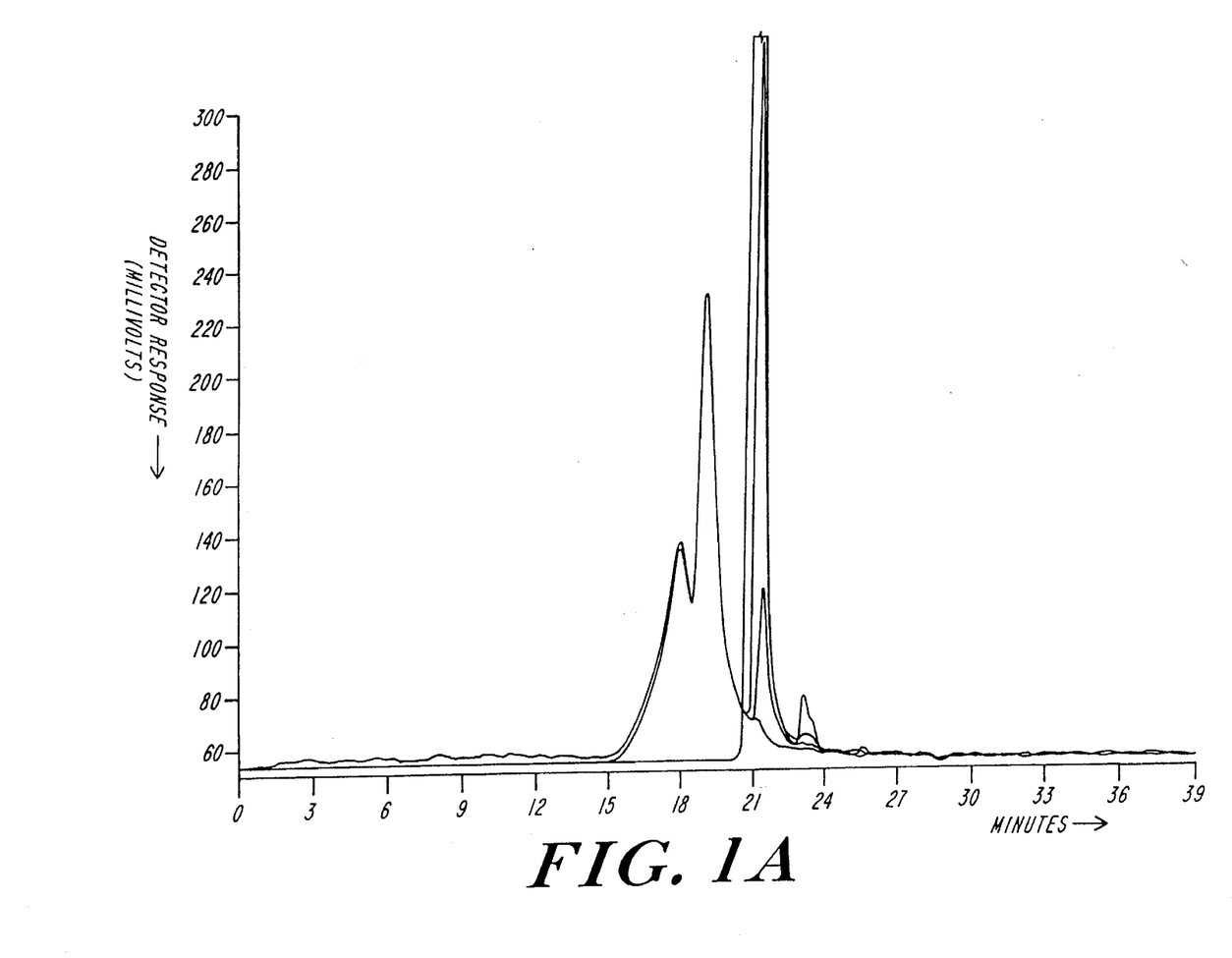
FIG. 1A is a chromatogram of UV absorption versus time at 210 nm of serum proteins and an oligonucleotide analog separated by size exclusion chromatography.
Figure 1B:
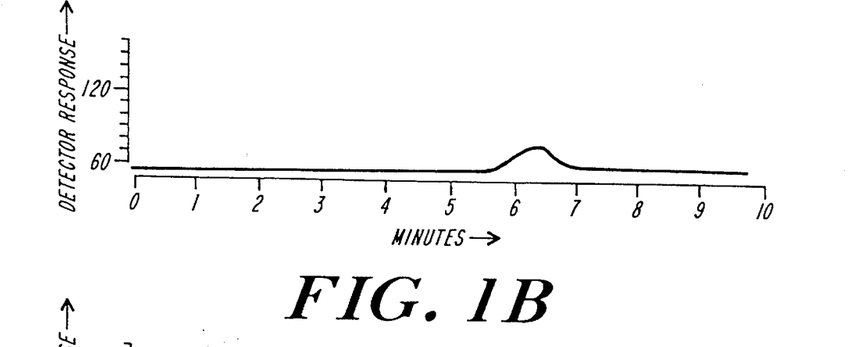
FIG. 1B is a chromatogram of UV absorption versus time at 210 nm of protein EcoSSB which migrates through a size exclusion chromatography column as a single broad peak.
Figure 1C:
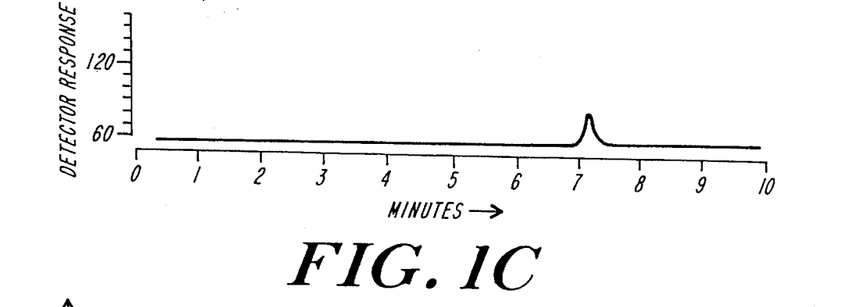
FIG. 1C is a chromatogram of UV absorption versus time at 210 nm of phosphodiester linked DNA which migrates through a size exclusion chromatography column as a single peak.
Figure 1D:
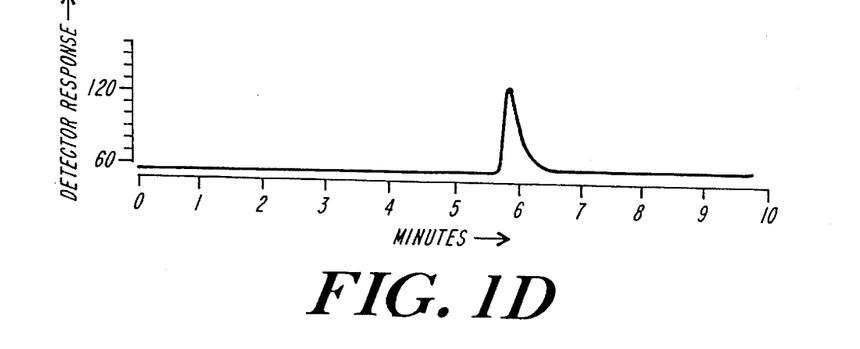
FIG. 1D is a chromatogram of UV absorption versus time at 210 nm of phosphodiester-linked DNA and protein EcoSSB which migrates through a size exclusion chromatography column as an adduct.
Figure 1E:
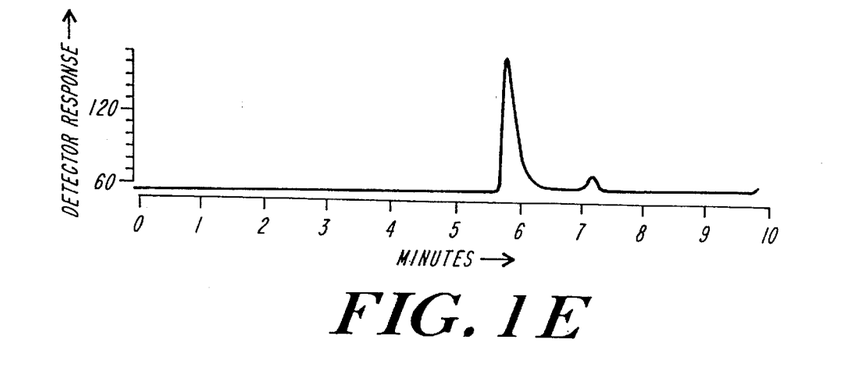
FIG. 1E is a chromatogram of UV absorption versus time at 210 nm of excess phosphodiester-linked DNA and protein EcoSSB which migrates through a size exclusion chromatography column as both an adduct and as unbound DNA.

The scientific basis of the method relies on the relatively weak binding of charged oligonucleotide analogs to proteins in biological fluid. For example, when charged oligonucleotides in combination with serum proteins are subjected to size exclusion chromatography (which separates molecules according to size), two major species are resolved (see FIG. 1A). Serum proteins are heavier (left 2 peaks) and thus run slower than the oligonucleotide analog (right peak). These results are expected if the oligonucleotide and proteins do not bind or bind very weakly to each other forming an adduct which migrates through and is eluted from the column at the same time (see FIG. 1D in which 1 part DNA to 1 part phosphodiester-linked protein migrates as a single peak). When at least 3 parts phosphodiester-linked DNA are run to 1 part protein, a lighter DNA peak begins to form as shown in FIG. 1E). These results suggest that proteinase K is not necessary to obtain high recoveries of oligonucleotide analog (as in the EcoSSb-Pd(T)$_{20}$ binding study shown in FIGS. 1B–1E, where the protein-DNA binding is very strong).

The method of the invention also relies on the relatively strong binding of such analogs to anion exchange resins. For example, deoxyribonucleotides with phosphorothioate internucleotide linkages have a much higher affinity for anion exchange resins than do phosphodiester-linked deoxyribonucleotides. This difference is due to the higher charge density on the phosphodiester non-bridging oxygen. The sulfur is more delocalized and therefore the charge density on it is lower. This theory is supported by sulfur is more delocalized and therefore the charge density on it is lower. This theory is supported by the higher acidity of phosphorothioates and their stronger ionic bond to tetraalkylammonium ligands.

Similarly, other charged oligonucleotides having backbone linkages with stronger or weaker charge densities than the phosphodiester oxygen are thus capable of being monitored by this method. Such oligonucleotides include, but are not limited to, phosphorodithioates.

An additional benefit of this method is the ability to detect oxidation changes to the original charged oligonucleotide analog. For example, in the case of a phosphorothioate, replacement of even one sulfur group with an oxygen results in a dramatic change in retention time. Previous methods have been unable to provide information concerning changes in the degree of oxidation of the oligonucleotide.

The biological fluid that can be tested by this method includes any sample from an organism, culture, or tissue which has been treated with an oligonucleotide analog for any number of purposes, including antisense or gene therapy. Examples of biological fluids include any body fluid such as serum, plasma, urine, semen, seminal fluid, lacrimal secretions, sweat, mucous secretions, cerebrospinal fluid, synovial fluid, and saliva. Such fluids are sampled from the body by normal medical procedures.

Other biological fluids which also can be monitored by this method include the extract of a cell such as a plant, bacterial, animal, or fungal cell. Cell extracts may be prepared according to any known method including, for example, mechanical or enzymatic sheering or disruption of cell membranes (and walls in the case of plants and fungal spores), and then separation of the extract from the particular matter via, e.g., differential centrifugation (see, e.g., *Current Protocols in Molecular Biology* (Ausubel et al., eds.) John Wiley & Sons, New York (1990) 2:2.2). Oligonucleotide analogs in body tissues may also be monitored by this method. Tissues are monitored as extracts obtained as described above.

Because the charged oligonucleotide analogs do not bind significantly to biological fluid proteins, direct injection of oligonucleotide-containing biological fluid into and through the anion exchange resin is quantitatively possible. However, it may be necessary to filter the fluid sample before analysis to remove large aggregates or particulate matter. Useful filters include a 0.2 µm cellulose triacetate membrane through which aliquots of samples to be tested can be forced via a syringe. The recovery of oligonucleotide analog from the cellulose triacetate filters has been assessed by comparing the peak area of a sample before and after filtration. The peak area remained unchanged indicating there was no loss of DNA to the filter.

In the method of the invention, a biological fluid sample thus obtained and prepared is contacted with an anion exchange resin. Under the experimental conditions, nucleic acids bind more strongly to the resin than do proteins, carbohydrates, or other components of the biological fluid being tested. In addition, charged oligonucleotide analogs more highly charged than phosphodiester-linked oligonucleotides bind more strongly to the resin than do phosphodiester-linked oligonucleotides. One useful resin is a strong anion exchange resin such as quaternary alkylamine, which is commercially available from any number of chromatography suppliers including Dionex Corp. (Sunnyvale, Calif.; 13 µm Dionex Nucleopak PA-100) or PerSeptive Biosystems (Cambridge, Mass.).

Another useful resin is a weak anion exchange resin such as diethylaminoethyl or polyethyleneimine. However, if such a weak anion exchange resin is to be used, the pH of the biological fluid sample to be tested must be adjusted with a buffer having a pH of about 6.9 to 7.0 such that the ultimate pH of the fluid sample is the same (pH 6.0 to 7.0). Useful buffers for this purpose include Tris-HCl phosphate, and acetate buffers, pH 6.0 to 7.0.

The biological fluid sample is put in contact with the resin for a time sufficient to enable any charged oligonucleotides in the sample to adsorb to the positively charged resin. This step is preferably carried out at from about 40° C. to 65° C. as higher temperatures may result in protein precipitation and lower temperatures may result in decreased column efficiency. Adsorbance occurs quickly and easily so that physical contact with the resin is all that is required. All unadsorbed material is then washed away or kept for further analysis and quantitation if this material contains a desired oligonucleotide or oligonucleotide analog. The adsorbed oligonucleotide analog is desorbed from the resin with a buffer having a salt concentration of about 1M to 2.5M, a pH in the range of about 6.5 to 7.5, and at a temperature of about 40° C. to 65° C. This buffer preferably includes a soft anion such as bromide, chloride, or thiocyanide. Preferable salts including such soft anions include lithium bromide, lithium chloride, potassium bromide, potassium chloride, ammonium bromide, and ammonium chloride. A buffer containing these salts at a concentration of about 2M is particularly useful.

The contacting and desorbing steps may be carried out in a number of ways, chromatographic and solid phase extraction methods being representative thereof.

One useful chromatographic method includes high pressure liquid chromatography (HPLC). Using HPLC, the method of the invention can be performed with, for example, a 20×2 mm inner diameter stainless steel guard column hand packed with the anion exchange resin of choice. 2 µm titanium frits are placed on either end of the column to keep the resin in place. This analytical column is inexpensive to run as it can be reused for over one hundred (100) µl injections of biological fluid without an unacceptable loss in peak shape or retention times. Since organic solvents generally cause proteins to denature and precipitate, a completely aqueous mobile phase is used. This also greatly reduces the cost of waste disposal. The HPLC system should have temperature control for the column compartment and minimal mixing volumes or gradient lag (e.g., 420 µl ) for the high pressure gradient mixer.

Figure 2A:
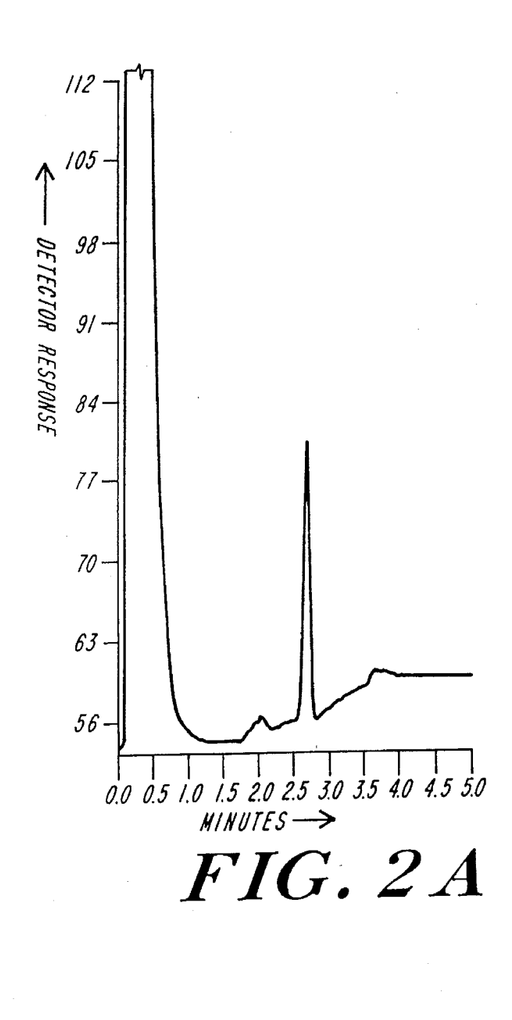
FIG. 2A is a chromatogram at $A_{270}$ of a monkey serum sample taken 14 days after intravenous administration of the oligonucleotide analog.
Figure 2B:
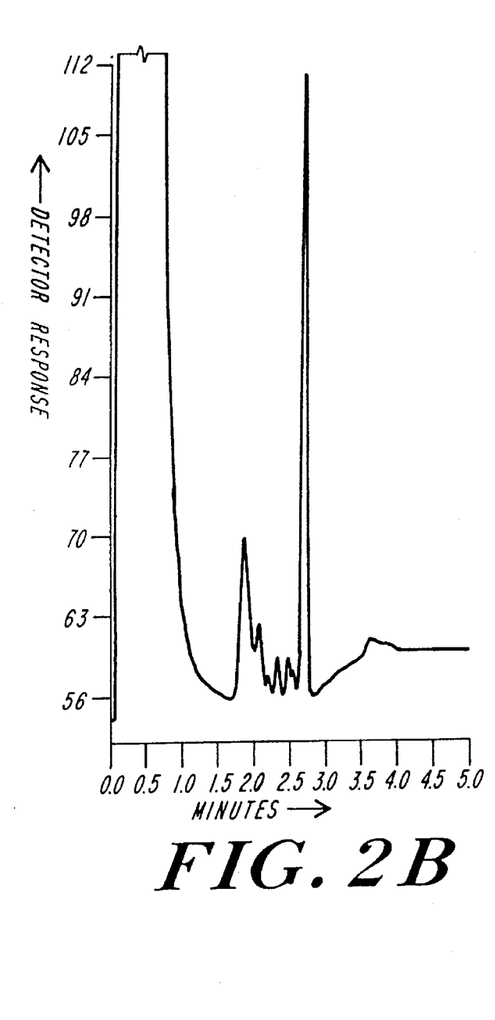
FIG. 2B is a chromatogram of UV absorption versus time at 270 nm of 5 ppm oligonucleotide analog standard in human serum.

The fluid sample is then injected directly into the HPLC column. Proteins and native nucleic acids that weakly bind to the anion exchange resin are removed by passing low concentrations (e.g., 250 mM HBr) of salt through the resin. The charged analog and its metabolites are then eluted from the column, and the concentration determined by some mode of detection. For example, the oligonucleotide analogs desorbed from the resin can be detected via UV absorbance at 270 nm using a spectrophotometer or other variable wavelength detector. The detector response is calibrated using known concentrations of analog (spiked) in the biological fluid being measured. This HPLC method is demonstrated as follows:

Oligonucleotide analog standards in buffer and serum are analyzed by HPLC having a throughput of 5 min per sample. Frozen plasma aliquot samples taken from monkeys at different times after injection with oligonucleotide analog are thawed, filtered and injected into quaternary-amine resin in 250mM LiBr, pH 7.0 at 0.7 ml/minute for 0.5 minutes and then brought to 2000 mM LiBr over 2 minutes and held for 1 minute. The flow rate is then doubled and the buffer composition returned to 250 mM LiBr. After 1 minute, the flow is returned to 0.7 ml/minute and the next sample is injected. Representative results are shown in FIGS. 2A wherein plasma from monkeys injected with 25 mg/kg oligonucleotide analog was sampled 15 minutes after animal injection. FIG. 2B is a 5 ppm standard oligonucleotide analog spiked into human serum. The results obtained from plasma sampled from monkeys injected intravenously (10 ml of 4 mg/ml analog solution over 10 min.) or subcutaneously (20 mg/ml analog solution using a 5–10 min. injection time) are summarized in TABLES 1A, 1B, and 2.

TABLE 1A

INFUSION RATE VS. ANALOG SERUM LEVELS

| | | | Dosage by i.v. over 10 min (ppm, µg/ml) | | | | | | | | | | |
|---|---|---|---|---|---|---|---|---|---|---|---|---|---|
| Animal I.D. | Dosage | | -5 | 5 | 10 | 20 | 40 | 60 | 90 | 120 | 240 | 18 | 48 | 72 |
| No. (R) | Grp # | (mg/kg) | min | min | min | min | min | min | min | min | min | hrs | hrs | hrs |
| | Postdose Time → | | 0 | 0 | 0 | 10 min | 30 min | 50 min | 80 min | 110 min | 230 min | ~18 hrs | ~48 hrs | ~72 hrs |
| 125E | 1 | 0 | 0 | 0 | 0 | 0 | 0 | 0 | 0 | 0 | 0 | 0 | 0 | 0 |
| 522 | 0 | 0 | 0 | 0 | 0 | 0 | 0 | 0 | 0 | 0 | 0 | 0 | 0 | |
| 2017 | 2 | 1.25 | 0 | 12 | —* | 17 | 13 | 11 | 7 | 6 | 1 | 0 | 0 | 0 |
| 67F | 2 | 1.25 | 0 | 11 | 22 | 17 | 13 | 10 | 4 | 0 | 0 | 0 | 0 | 0 |
| 1831 | 3 | 5 | 0 | 45 | 70 | 54 | 45 | 39 | 31 | 26 | 3 | 0 | 0 | 0 |
| 512 | 3 | 5 | 0 | 44 | 80 | 67 | 53 | 43 | 33 | 26 | 9 | 0 | 0 | 0 |
| 1133 | 4 | 20 | 0 | 91 | 139 | 141 | 77 | 61 | 59 | 50 | 34 | 0 | 0 | 0 |
| 1058 | 4 | 20 | 0 | 144 | 195 | 156 | 92 | —** | | | | | | |

*sample lost
**animal died

TABLE 1B

INFUSION RATE VS. ANALOG SERUM LEVELS

| | | | Dosage by i.v. over 10 min (ppm, µg/ml) | | | | | | | | | | |
|---|---|---|---|---|---|---|---|---|---|---|---|---|---|
| Animal I.D. | Dosage | | -5 | 30 | 60 | 90 | 120 | 150 | 3 | 50 | 18 | 48 | 72 |
| No. (R) | Grp # | (mg/kg) | min | min | min | min | min | min | min | min | min | hrs | hrs |
| | Postdose Time → | | 0 | 0 | 0 | 0 | 0 | 30 min | 1 hr | 3 hrs | 16 hrs | 46 hrs | 70 hrs |
| 2027 | 5 | 0 | 0 | 0 | 0 | 0 | 0 | 0 | 0 | 0 | 0 | 0 | 0 |
| 24F | 5 | 0 | 0 | 0 | 0 | 0 | 0 | 0 | 0 | 0 | 0 | 0 | 0 |
| 1153 | 6 | 5 | 0 | 12 | 22 | 29 | 34 | 29 | 27 | 10 | 0 | 0 | 0 |
| 40E | 6 | 5 | 0 | 18 | 32 | 41 | 46 | 37 | 32 | 8 | 0 | 0 | 0 |
| 1565 | 7 | 20 | 0 | 64 | 72 | 93 | 111 | 75 | 61 | 42 | 0 | 0 | 0 |
| 1086 | 7 | 20 | 0 | 64 | 88 | 101 | 111 | 80 | 72 | 37 | 0 | 0 | 0 |
| 1159 | 8 | 80 | 0 | 180 | 284 | 413 | 445 | 263 | 178 | 79 | 12 | 0 | 0 |
| 1552 | 8 | 80 | 0 | 193 | 324 | 381 | 395 | 219 | 190 | 82 | 7 | 0 | 0 |

TABLE 2

ADMINISTRATION ROUTE vs. ANALOG SERUM LEVELS

| Animal I.D. | Dosage | | Concentration in (ppm, µg/ml) | | | | | | | | | | | | |
|---|---|---|---|---|---|---|---|---|---|---|---|---|---|---|---|
| | | | 0 | 5 | 15 | 30 | 60 | 2 | 4 | 8 | 12 | 24 | 48 | 72 | 96 |
| No. (R) | Grp # | (mg/kg) | min | min | min | min | min | min | min | min | min | hrs | hrs | hrs | hrs |
| 1282 | 1 | $1^1$ | 0 | 15 | 13 | 10 | 6 | 1 | .15 | 0 | 0 | 0 | 0 | 0 | 0 |
| 1171 | 1 | $1^1$ | 0 | 16 | 14 | 11 | 7 | 2 | .17 | 0 | 0 | 0 | 0 | 0 | 0 |
| 1107 | 1 | $1^1$ | 0 | 16 | 13 | 10 | 6 | .83 | 0 | 0 | 0 | 0 | 0 | 0 | 0 |
| 1196 | 2 | $5^2$ | 0 | 81 | 69 | 57 | 46 | 29 | 5 | .14 | .07 | 0 | 0 | 0 | 0 |
| 2049 | 2 | $5^2$ | 0 | 72 | 60 | 50 | 40 | 25 | 4 | .14 | .07 | 0 | 0 | 0 | 0 |
| 2025 | 2 | $5^2$ | 0 | 95 | 78 | 65 | 54 | 36 | 7 | .18 | 0 | 0 | 0 | 0 | 0 |
| 1258 | 3 | $5^2$ | 0 | .84 | 3.1 | 7.4 | 15 | 25 | 22 | 1.8 | .29 | 0 | 0 | 0 | 0 |
| 517 | 3 | $5^2$ | 0 | .61 | 2.3 | 5.0 | 9.4 | 16 | 18 | 3.4 | .30 | 0 | 0 | 0 | 0 |
| 2080 | 3 | $5^2$ | 0 | .54 | 1.8 | 3.3 | 5.9 | 13 | 15 | 4.0 | .20 | 0 | 0 | 0 | 0 |
| 1166 | 4 | $25^2$ | 0 | 2.3 | 14 | 37 | 67 | 91 | 65 | 44 | 18 | 0 | .21 | 0 | 0 |
| 2047 | 4 | $25^2$ | 0 | 2.0 | 7.7 | 18 | 37 | 61 | 77 | 56 | 29 | 0 | .14 | 0 | 0 |
| 506 | 4 | $25^2$ | 0 | 1.9 | 12 | 30 | 45 | 78 | 90 | 50 | 21 | 0 | .13 | 0 | 0 |

[1] intravenous
[2] subcutaneous

Figure 3:
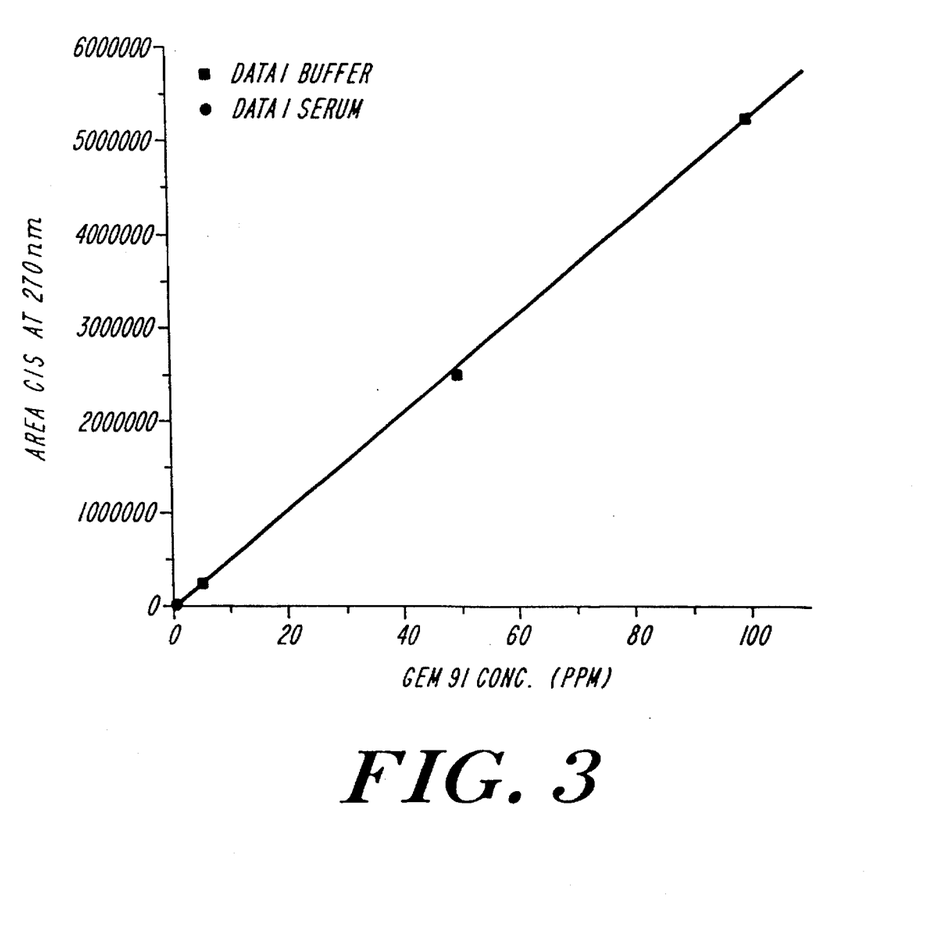
FIG. 3 is a plot of the linear range of detection and recovery of oligonucleotide analog at 50° C., pH 7.0.

The recovery of oligonucleotide analog from serum is addressed by creating a calibration curve in buffer and in serum and comparing the slopes of the detector response vs. the concentration injected. This is shown in FIG. 3 where throughput is 5 min/sample, standards in buffer are squares and in serum are circles. The calibration curve for these gradient elution conditions is linear from 200 parts per billion (ppb) to 200 parts per million (ppm) and shows very high recovery of the analog in this range. In addition, the recovery of analog from the serum and buffer is virtually identical under these conditions (i.e., the slopes of the calibration curves shown in FIG. 2A overlap). These data indicate the standard analog spiked into human serum behaves similarly to analog already present in the monkey serum. Data generated from two bioavailability studies shows that 100 µl aliquots of filtered serum or urine are required to accurately quantify concentrations as low as 100 ppb analog. The linear range of detection is the detection limit to approximately 200 ppm. However, a narrow bore column shows signs of overload (non-gaussian peak shape) at concentrations above 50 ppm. Thus, samples greater than 20 ppm are diluted with 25 mM Tris buffer, pH 7, and then analyzed. The concentration interpolated from the calibration curve is then multiplied by the dilution factor to obtain the initial sample concentration. Larger volumes can be injected and the on-line preconcentration phenomena can be used to attain very low concentration detection limits. The concentration detection limit for this system is 50 ng/ml (assuming a 200 µl injection).

Alternatively, oligonucleotide analogs can be detected and quantitated by hybridizing them to a complementary oligonucleotide probe which has been labeled with, e.g., radioactive elements such as $^{32}$P, or $^{35}$S, or any other conventional label such as a fluorescent compound like rhodamine or fluorescein, a chemiluminescent label, biotin or enzymes (see, e.g., patent application Ser. Nos. 08/002,786 and 08/056,363, the disclosures of which are herein incorporated by reference).

Briefly, such labels may be incorporated directly onto the complementary oligonucleotide probe. Hybridization and wash conditions must be set for the type of oligonucleotide analog being monitored. For example, for oligonucleotides having ionic internucleotide linkages, such as oligonucleotide phosphodiesters or phosphorothioates, incubation in 6×SSC, 3 to 16 hours of hybridization at 37° C., followed by two 5 to 10 minute washes in 6×SSC at room temperature is appropriate for detection of a 25-mer oligonucleotide with 56% G+C content, using a 25-mer probe having 62% G+C content. At higher stringencies, similar target oligonucleotide may not be detected, whereas at lower stringencies, background hybridization may obscure the signal. For oligonucleotides having nonionic modified internucleotide linkages or lower G+C content, lower stringency (e. g., lower temperatures, higher salt concentrations) may be helpful. For longer oligonucleotides or for oligonucleotides having higher G+C content or RNA components, increases in stringency (e.g., higher temperatures, lower salt concentrations, and/or presence of hydrogen bond competitors such as formamide) may be useful. The relationship between melting temperatures and various modified internucleotide linkages has been well described (see e.g., FIG. 9 of U.S. Pat. No. 5,149,798, the teachings of which are hereby incorporated by reference). Following washing, the membrane is dried and the signal is detected by conventional means, such as fluorescence detection, β-emission detection, chemiluminescence detection, or autoradiography.

The contacting and desorbing steps of the invention may also be carried out using solid phase extraction techniques. This off-line procedure includes packing the resin into a flow-through tube or column, washing it with elution buffer, conditioning it with a low salt buffer, and then adhering the biological fluid sample thereto via direct contact. Unwanted, weakly retained materials are washed out with buffers have a salt concentration greater than the sample solution but weaker than that needed to remove the oligonucleotide analogs. The oligonucleotide analogs are removed from the resin with the appropriate elution buffer and are described above (see, e.g., *Supelco Guide to Solid Phase Extraction*, 2d Ed., Bellefonte, PA, Form 97857B).

The following examples illustrate the preferred modes of making and practicing the present invention, but are not meant to limit the scope of the invention since alternative methods may be utilized to obtain similar results.

EXAMPLES

1. Preparation of Oligonucleotide Analogs

The oligonucleotide analog standard used in the animal assay is a 25 mer phosphorothioate complementary to the gag region of the HIV-1 genome spanning nucleotides 324–348 (SEQ ID NO:1). This oligonucleotide is prepared according to known synthetic protocols, such as the triester method, oxidation of phosphite triesters with sulfur, the standard amidite method, the single step sulfurization modification of the H-phosphonate by a modification of the amidite method, or by a modification of the H-phosphonate method (see Uhlmann et al. (1990) *Chem. Rev.* 90:543–585) for a general review of synthetic methods of synthesizing many charged oligonucleotide analogs). The oligonucleotide is subjected to semi-preparative HPLC and then desalted on a C18 column (Millipore, Milford, MA) with a triethylammonium acetate buffer and 10–60% acetonitrile gradient. The oligonucleotide is lyophilized and diluted in 1 ml of 20 mM Tris, 2 mM EDTA, pH 8.5. A UV absorbance reading of $A_{267}$ of an aliquot of this stock solution is taken and the OD reading multiplied by 40.8 μg/OD to yield the concentration in parts per million (ppm). Dilutions of this stock solution (and other serial dilutions) are made directly into serum or other body fluid.

2. Bioavailability Studies in Animals

The test materials are administered to adult Rhesus monkeys through a catheter placed in a cephalic or saphenous vein (if the saphenous vein is used it will the vein contralateral to the arterial and venous recording site). The infusions are accomplished by use of a Harvard Infusion Pump (Cambridge, MA). The test sample was dissolved in the control article at a concentration calculated to deliver the dose shown below at a rate of 0.42 ml/min. Prior to the infusion, the catheter is filled with extra dosing material to ensure that the animal receives the appropriate dose. Each animal received a single infusion.

Two types of studies are performed in which the administration route of oligonucleotide analog into Rhesus monkeys is varied and the bioavailability of oligonucleotide analog assessed. The first type of study investigates the difference in bioavailability of oligonucleotide analog using slow (120 minutes) and fast (10 minutes) intravenous administration. The second type of study investigates the difference in bioavailability of oligonucleotide analog by fast intravenous (10 minutes) and subcutaneous administrations (5–10 seconds).

The test material is administered to each animal in Groups 1–4 for 10 minutes and to each animal in Groups 5–8 for 120 minutes as shown in TABLE 3.

TABLE 3

| Dose Group | Number of Animals | Total Dose (mg/kg) | Duration Infusion | Rate of Infusion (mg/kg/hr) |
| --- | --- | --- | --- | --- |
| 1 | 3 | 0 | 10 min. | 0 |
| 2 | 3 | 1.25 | 10 min. | 7.5 |
| 3 | 3 | 5.00 | 10 min. | 30.0 |
| 4 | 3 | 20.00 | 10 min. | 120.0 |
| 5 | 3 | 0 | 120 min. | 0 |
| 6 | 3 | 5.00 | 120 min. | 2.5 |
| 7 | 3 | 20.00 | 120 min. | 10.0 |
| 8 | 3 | 80.00 | 120 min. | 40.0 |

Dosing is discontinued when obvious signs of toxicity develop. Additional dose groups may be added in order to clearly demonstrate toxicity at the highest dose level and no effect at the lowest dose level for both the rapid and slow infusion groups.

Biological fluids samples are then taken. To test serum or plasma sample, blood is collected in heparinized tubes and centrifuged to separate the cells from the plasma. In addition, urine, saliva, mucous secretions, lacrimal secretions, cerebrospinal fluid, seminal fluid, synovial fluid, and semen are also be collected for analysis or frozen for analysis at a later time.

3. Standard and Sample Preparation

Standards are prepared as follows. A stock solution of sample oligonucleotide analog is prepared by dissolving 4 mg of sample in 1 ml of 20 mM Tris buffer, pH 7. The DNA content is determined spectrophotometrically at 267–270 nm. The sample is quantitatively diluted to obtain an absorbance of between 1 and 20 D. The absorbance is multiplied by 40.8 μg/OD and the dilution factor to obtain the concentration in ppm (μg/ml). Aliquots of this stock solution are spiked into pooled human serum, plasma, saliva, mucous secretions, lacrimal secretions, semen, synovial fluid, cerebrospinal fluid, urine, or cell extract samples at concentrations which bracket the expected biological fluid levels of sample oligonucleotide analog. Expected levels do not exceed the amount of oligonucleotide analog administered to the organism.

Frozen biological fluid samples are allowed to thaw and are stored at 4° C. until time of analysis. Samples (about 1 ml) are vortexed to assure homogeneity and then passed through a disposable syringe-tip 0.2 μm cellulose triacetate filter into labelled 1.5 ml eppendorf tubes. The samples are placed in a queue at room temperature to be analyzed by HPLC. At present, 100 μl aliquots of filtered serum, plasma, urine, saliva, semen, lacrimal secretions, or other biological fluid samples are required to accurately quantify concentrations as low as 100 ppb 25 mer oligonucleotide analog. The linear range of detection is the detection limit to approximately 50 ppm. Samples greater than 20 ppm are usually diluted with Tris buffer and rerun. Larger volumes can be injected and the on-line preconcentration phenomena can be used to attain very low concentration detection limits. Samples which exceeded 50 ppm oligonucleotide analog concentration are quantitatively diluted with 20 mM Tris buffer, pH 7, and reanalyzed. For serum levels above 1 ppm sample oligonucleotide analog, 25 μl of sample are injected into the HPLC. For serum samples below 1 ppm, 100 μl are injected.

4. HPLC

A 20×2 mm inner diameter hand-packed stainless steel analytical guard column (UpChurch Scientific, Oak Harbor, Wash.) is packed with 13 μm stationary phase resin (Dionex Nucleopak PA-100 (Sunnyvale, Calif.) sandwiched between 2 μm titanium frits. The column is thermostated at 50° C. The mobile phase column buffers are (A) 250 mM Tris-HBr, pH 7, and (B) 2M LiBr, 25 mM Tris-HBr, pH 7. Both buffers are filtered through a 0.45 μm nylon membrane.

To determine system suitability, water blanks, biological fluid blanks and oligonucleotide analog standards in specific biological fluids are run periodically with the samples. These standards calibrate the detector response versus oligonucleotide analog concentration and are used as markers of system suitability. A representative analysis queue is as follows: (1) blank; (2) biological fluid blank; (3) oligonucleotide standards (e.g., three concentrations in the window of interest); (4) 10 samples; (5) oligonucleotide analog standards (at three concentrations in the window of interest); (6) water blank; (7) 10 samples; and (8) oligonucleotide analog standards (at three concentrations in the window of interest).

The samples are injected into an initial mobile phase composition of 250 mM LiBr, pH 7 at 0.7 ml/min at 50° C. for 0.5 minutes and then brought to 2M LiBr over 2 minutes and held for 1 minute. The flow rate is then doubled and the mobile phase composition returned to 250 mM LiBr at 1.5 ml/min for 1 minute. Finally, the flow is decreased to 0.7 ml/min and the next sample is injected. Using this profile, a sample can be analyzed every 5 minutes (see FIGS. 2A and 2B).

To determine if the column should be replaced, the retention time of the standards is monitored. The retention time shifts with number of injections onto the column. When a retention shift of 0.2 min/3.6 min is found, which is usually concomitant with an increase in pressure, the column is replaced.

5. Detection and Quantitation by UV Absorbance

The sample concentration is determined by external standard calibration. The UV absorbance at 270 nm is plotted versus the concentration of oligonucleotide analog in the standards. A least squares regression is performed. A minimum correlation coefficient of 0.99 is required for system suitability. If this is not met, the standards must be prepared again and analyzed. Standard solutions of oligonucleotide analog are prepared fresh daily and kept at room temperature during analysis.

6. Detection by Labelled Oligonucleotide Probe

For preparation of radiolabelled oligonucleotide probe, an oligonucleotide complementary to the oligonucleotide injected into the sample or used to spike the blood, urine or tissue samples is labelled with $^{32}$P at its 5' end in a reaction mixture containing 100 ng oligonucleotide (5 µl), 3 µl [gamma-$^{32}$P] ATP (3,000 Ci/mmole at 10 mCi/ml), 1 µl 10×kinase buffer, and 1 µl T4 polynucleotide kinase (8–10 units/µl) at 37° C. for 30 minutes, then heated to 65° C. for 3 minutes. Labelled oligonucleotide is then precipitated with 0.4M NH$_4$OAc and ethanol and resuspended in 50 µl of H$_2$O.

Alternatively, nonradioactive chemiluminescent probes are prepared using the Genius 5™ Oligonucleotide Tailing Kit (Boehringer Mannheim) according to the manufacturer's instructions. One µg oligonucleotide is 3'-tailed with Digoxygenin-11dduTP/dATP (DIG-11-dduTP/dATP) in the presence of terminal transferase. The 20 µl reaction mixture volume contains 4 µl 5×reaction buffer (1M potassium cacodylate, 125 mM Tris-HCl, 1.25 mg/ml bovine serum albumin, pH 6.6 at 25° C.), 4 µl 25 mM cobalt chloride, 100 picomoles oligonucleotide, 1 µl 1 mM DIG-11-dduTP (2', 3' dideoxyuridine-5' triphosphate coupled to digoxygenin via an 11 atom spacer arm), and 50 units terminal transferase. The reaction mixture is incubated at 37° C. for 15 minutes and then placed on ice. One µl 20 mg/ml glycogen and 1 µl 200 mM EDTA (pH 8.0) are added to the reaction mixture, which is then precipitated by adding 0.1 volume 4M lithium chloride and 2.5 volumes of chilled ethanol, and then mixed and incubated at −70° C. for 30 minutes. The oligonucleotide is pelleted and the pellet was washed with 70% ethanol, and resuspended in 30 µl 10 mM Tris-HCl (pH 7.0–8.0)/1 mM EDTA/1% SDS.

One piece each of nylon membrane (Zeta Probe™, BiO Rad)) and Whatman 3 MM paper are wetted in 10 ×SSC. Wetted Whatman paper is placed in a dot blot apparatus (Minifold II™, Schleicher & Schuell) and the wetted nylon membrane is placed atop the Whatman paper. The multiple-well lid is placed on the apparatus and latched in place, then the apparatus is hooked up to a vacuum source. Wells are rinsed with 100µl 20×SSC, then samples prepared according to Example 1 are added in 10 µl TE+40 ml 20×SSGto the wells. Wells are then rinsed with 100 µl 20× SSC. Vacuum is then turned off and the nylon membrane removed. The nylon membrane is then exposed for 10 minutes to short wave (<300 nm) UV light at a distance of 10 cm with the topside of the membrane facing the UV source to cross-link nucleic acids to the membrane.

The membrane is prehybridized in 10 ml hybridization buffer (1M NaCl/1% SDS/10% dextran sulfate and 150 µg/ml tRNA) for 1 to 3 hours at 37° C. To the membrane in hybridization solution is added labelled oligonucleotide probe diluted with 3 µg/ml final concentration unlabelled complementary oligonucleotide (5×10$^5$ cpm/ml; 250 ng/ml final concentration of probe) and incubation was continued for 3–16 hours at 37° C. The membrane is washed twice (5–10 minutes per wash) in 6×SSC, then dried at room temperature.

Detection of probe specifically bound to the membrane is carried out as follows. The membrane is exposed to X-ray film, which is then developed and subjected to scanning densitometry, with comparison to samples of known quantities of oligonucleotide that had been directly blotted to the membrane.

These results demonstrate that the method according to the invention can detect oligonucleotides present at a concentration as low as 3 ng/ml in body fluids or tissues. In addition, the method according to the invention can be used to quantitate oligonucleotides present in body fluids or tissues.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

---

What is claimed is:

1. A method for detecting oligonucleotides present in a biological fluid at a concentration of at least 3 ng/ml, the oligonucleotides having the same or different lengths or sequences, and having phosphorothioate internucleotide linkages, the method comprising the steps of:
   (a) contacting a biological fluid sample with a strong anion exchange resin comprising a quaternary alkylamine in the range of 40° C. to 65° C. for a time sufficient to enable oligonucleotides in the sample to adsorb to the resin;
   (b) desorbing the oligonucleotides from the resin with a buffer having a salt concentration in the range of 1M to 2.5M and a pH in the range of 6.5 to 7.5, the desorption being performed in the range of 40° C. to 65° C.; and
   (c) detecting the oligonucleotide released from the resin.

2. The method of claim 1 wherein contacting step (a) comprises contacting a biological fluid sample with the resin, the sample being selected from the group consisting of serum, plasma, urine, semen, seminal fluid, lacrimal secretions, saliva, cerebrospinal fluid, sweat, cell extracts, and tissue extracts.

3. The method of claim 1 wherein contacting step (a) further comprises mixing the sample with a buffer comprising a salt concentration in the range of 100 mM to 300 mM.

4. The method of claim 3 wherein the buffer comprises a salt concentration of about 250 mM.

5. The method of claim 1 comprising the additional step of filtering the biological fluid sample before contacting step (a).

6. The method of claim 1 wherein desorbing step (b) comprises eluting the oligonucleotides from the resin with a buffer containing a soft anion selected from the group consisting of bromide, chloride, and thiocyanide.

7. The method of claim 6 wherein the buffer comprises a salt selected from the group consisting of lithium bromide, lithium chloride, bromide, chloride, and thiocyanide, potassium bromide, potassium chloride, ammonium bromide, and ammonium chloride.

8. The method of claim 1 wherein desorbing step (b) comprises eluting the oligonucleotides from the resin with a buffer comprising 2M salt.

9. The method of claim 1 wherein desorbing step (b) comprises eluting the oligonucleotides from the resin with a fast salt gradient.

10. The method of claim 1 wherein contacting step (a) and desorbing step (b) comprise subjecting the sample to high pressure liquid chromatography.

11. The method of claim 1 wherein contacting step (a) and desorbing step (b) comprise subjecting the sample to solid phase extraction.

12. The method of claim 1 wherein detecting step (c) comprises detecting the oligonucleotides by UV absorbance at 270 nm.

13. The method of claim 1 wherein detecting step (c) comprises detecting the oligonucleotides by laser induced fluorescence.

14. The method of claim 1 wherein detecting step (c) comprises hybridizing to the eluted oligonucleotides a complementary oligonucleotide containing a detectable marker, removing any unhybridized oligonucleotides, and then detecting the marker on the hybridized complementary oligonucleotides.

15. The method of claim 13 wherein the marker is selected from the group consisting of a radioactive compound, a fluorescent compound, a chemiluminescent compound, biotin, and an enzyme.

16. A method for detecting oligonucleotides present in a biological fluid at a concentration of at least 3 ng/ml, the oligonucleotides having the same or differing lengths or sequences, and having phosphorothioate internucleotide linkages in biological fluids comprising the steps of:
   (a) contacting a biological fluid sample with an anion exchange resin in the range of 40° C. to 65° C. for a time sufficient to enable oligonucleotides in the sample to adsorb to the resin;
   (b) desorbing the oligonucleotides from the resin with a buffer having a salt concentration in the range of 1M to 2.5M and a pH in the range of 6.5 to 7.5, the elution being performed in the range of 40° C. to 65° C.;
   (c) detecting the oligonucleotide released from the resin; and
   (d) quantitating the detected oligonucleotide.

* * * * *

UNITED STATES PATENT AND TRADEMARK OFFICE
CERTIFICATE OF CORRECTION

PATENT NO. : 5,506,103
DATED : April 9, 1996
INVENTOR(S) : Aharon S. Cohen, Andre Bourque It is certified that error appears in the above-indentified patent and that said Letters Patent is hereby corrected as shown below:

In claim 16, line 39 - 40, after "with", "an anion exchange resin" should be changed to —a strong anion exchange resin comprising a quaternary alkylamine—.

Signed and Sealed this

Ninth Day of July, 1996

Attest:

BRUCE LEHMAN

*Attesting Officer*  *Commissioner of Patents and Trademarks*